US006211238B1

(12) United States Patent
Castillo et al.

(10) Patent No.: US 6,211,238 B1
(45) Date of Patent: Apr. 3, 2001

(54) PRESERVATIVE SYSTEM FOR TOPICALLY ADMINISTRABLE PHARMACEUTICAL COMPOSITIONS

(75) Inventors: Ernesto J. Castillo, Arlington; Steven Howard Gerson, Fort Worth; Wesley Wehsin Han, Arlington, all of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/400,133

(22) Filed: Sep. 21, 1999

Related U.S. Application Data
(60) Provisional application No. 60/105,820, filed on Oct. 27, 1998.

(51) Int. Cl.[7] .................. A61K 31/195; A61K 31/225
(52) U.S. Cl. .................. 514/563; 514/547; 514/556; 514/557; 514/560; 514/566; 514/568; 514/912; 424/659
(58) Field of Search .................. 514/556, 560, 514/563, 547, 568, 557, 566, 912; 424/659

(56) References Cited

U.S. PATENT DOCUMENTS

| | | | |
|---|---|---|---|
| 3,275,503 | 9/1966 | Marnett et al. | 167/22 |
| 4,380,637 | 4/1983 | Lindemann et al. | 548/112 |
| 4,485,029 | 11/1984 | Kato et al. | 252/106 |
| 4,911,920 | 3/1990 | Jani et al. | 424/78 |
| 5,000,868 | 3/1991 | Wittpenn, Jr. et al. | 252/106 |
| 5,093,126 | 3/1992 | Jani et al. | 424/428 |
| 5,494,937 | 2/1996 | Asgharian et al. | 514/772.3 |
| 5,504,113 | 4/1996 | Lucero | 514/554 |
| 5,520,920 | 5/1996 | Castillo et al. | 424/402 |
| 5,536,305 | 7/1996 | Yu | 106/18.33 |
| 5,540,918 | 7/1996 | Castillo et al. | 424/78.04 |
| 5,554,367 | 9/1996 | Ali et al. | 424/78.04 |
| 5,631,218 | 5/1997 | Allan et al. | 510/423 |
| 5,641,480 | 6/1997 | Vermeer | 424/70.24 |
| 5,741,817 | 4/1998 | Chowhan et al. | 514/561 |

FOREIGN PATENT DOCUMENTS

| | | |
|---|---|---|
| 0 194 097 A1 | 9/1986 | (EP) . |
| 0 243 145 | 4/1987 | (EP) . |
| 0 243 145 A2 | 10/1987 | (EP) . |
| 0 429 732 A1 | 6/1991 | (EP) . |
| 0 590 786 A1 | 4/1994 | (EP) . |
| 98/06381 | 2/1998 | (WO) . |
| 99/09947 | 3/1999 | (WO) . |

OTHER PUBLICATIONS

Aminosoap AR–12 Product Brochure from Ajinomoto .U.S.A., Inc., Torrance, CA (1997).
Aminosoap LYC–12S/LYC–12 Product Brochure from Ajinomoto .U.S.A., Inc., Torrance, CA (1997).
Amisoft Anionic Surfactant Product Brochures from Ajinomoto .U.S.A., Inc., Torrance, CA (1997).
Amilite GCK–12 Product Brochure from Ajinomoto .U.S.A., Inc., Torrance, CA (1997).
Hamposyl Surfactants Products Brochure from Grace Organic Chemicals, Lexington, MA (1992).
Cozzoli, Preservative–Free and Self–Preservig Cosmetics and Drugs: Principles and Practice, Marcel Dekker, Inc., New York, NY, (1997), Chapter 4 "The Role of Surfactants in Self–Preserving Cosmetic Formulas".

*Primary Examiner*—Rebecca Cook
(74) *Attorney, Agent, or Firm*—Patrick M. Ryan

(57) ABSTRACT

Anionic surfactants are used in conjunction with an antifungal acid and a chelating agent to preserve topically administrable pharmaceutical compositions without the need for a conventional preservative such as benzalkonium chloride.

19 Claims, No Drawings

PRESERVATIVE SYSTEM FOR TOPICALLY ADMINISTRABLE PHARMACEUTICAL COMPOSITIONS

This application claims priority to co-pending U.S. Provisional Application, Serial No. 60/105,820, filed Oct. 27, 1998.

BACKGROUND OF THE INVENTION

The present invention relates generally to the preservation of pharmaceutical compositions. In particular, the present invention relates to the use of certain anionic surfactants in combination with an antifungal acid and a chelating agent as a preservative system for topically administrable pharmaceutical compositions.

Multi-dose pharmaceutical products, particularly those intended for topical administration to the eyes, nose or ears, often contain or are required to contain a preservative. Such products are sterilized when manufactured, but contain preservatives to prevent or inhibit microbial growth in the event they are contaminated during use. The most common preservatives for topical, multi-dose ophthalmic products are quaternary ammonium preservatives, such as benzalkonium chloride and polyquaternium-1. Other known preservatives for topical, multi-dose ophthalmic products are chlorobutanol; chlorhexidine; parabens; and thimerosal (though thimerosal is not as common as it used to be, due to regulatory and environmental concerns related to the fact it contains mercury).

In some instances, preservatives alone are insufficient to meet regulatory standards for preservative efficacy. In such cases, preservative aids or adjuncts are used. Examples of preservative enhancing additives include the chelating agent EDTA (edetate disodium) and the antifungal agent boric acid. Additional examples of preservative enhancing additives include certain sarcosinate and lactylate surfactants.

U.S. Pat. No. 5,520,920 (Castillo, et al.) discloses the use of certain modified sarcosinates and lactylates to enhance antimicrobial effectiveness of ophthalmic compositions, particularly in the case where cationic preservatives otherwise bind to anionic polyelectrolytes. Representative modified sarcosinates include those sold under the Hamposyl® trade name, such as lauroyl sarcosine (Hamposyl® L), oleoyl sarcosine (Hamposyl® O), myristoyl sarcosine (Hamposyl® M), cocoyl sarcosine (Hamposyl® C), stearoyl sarcosine (Hamposyl® S), and pelargodoyl sarcosine (Hamposyl® P). Representative lactylates include sodium capryl lactylate (Pationic® 122A).

Anionic amino acid based surfactants other than the Hamposyl® surfactants are known and include, for example, those surfactants sold under the Amilite™ and Amisoft™ trade names (Ajinomoto Co., Inc., Tokyo, Japan). According to its product brochure, one such surfactant, Amilite™ GCK-12, is used as a detergent, a foaming agent, an emulsifier, a solubilizer and a dispersing agent. Examples of applications of Amilite™ GCK-12 include cosmetics and toiletries (hair shampoo and body wash), face wash (facial washing foam, facial washing creme, facial washing liquid and make-up remover), facial soap, toothpaste, bath soap, contact lens cleaners and household cleaners. Amisoft™ surfactants are described as gentle cleansers for the skin and hair. Major applications of Amisoft™ surfactants include facial and body cleansers, hair shampoos, syndet bars, body care and dermatological products.

Alternative preservative systems for topically administrable pharmaceutical compositions are desired, especially in those instances when conventional preservatives, such as benzalkonium chloride, are incompatible with other ingredients in the composition.

SUMMARY OF THE INVENTION

The present invention provides a preservative system for topically administrable pharmaceutical compositions. The preservative system consists essentially of i) at least one anionic surfactant of formula I or formula II below, ii) one or more pharmaceutically acceptable antifungal acids, and iii) one or more pharmaceutically acceptable chelating agents.

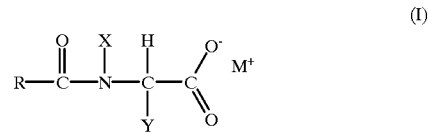

wherein: $R=C_8-C_{24}$ saturated or unsaturated hydrocarbon;
$X=H$ or $CH_3$;
$Y=H$, $(CH_2)_4NH_2$ or $(CH_2)_3NHC(NH_2)=N^+H_2$; and
$M^+=H$ or a pharmaceutically acceptable salt.

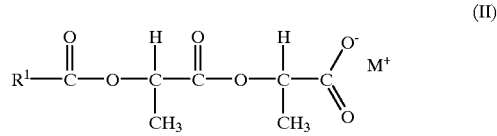

wherein: $R^1=C_8-C_{24}$ saturated or unsaturated hydrocarbon; and
$M^+$ is as defined above.

According to the present invention, topically administrable pharmaceutical compositions are preserved without the need for a conventional preservative ingredient. Thus, the compositions of the present invention do not contain any preservatives selected from the group consisting of quaternary ammonium preservatives, such as benzalkonium chloride, benzalkonium bromide, and polyquaternium-1; chlorhexidine; chlorobutanol; cetylpyridinium chloride; parabens; and thimerosal.

The present invention also relates to a method of preserving a topically administrable pharmaceutical composition, wherein the method comprises adding the preservative system described above to such composition.

Among other factors, the present invention is based on the finding that topically administrable pharmaceutical compositions can be preserved using a preservative system consisting of one or more anionic surfactants of formula I or II, one or more pharmaceutically acceptable antifungal acids and one or more pharmaceutically acceptable chelating agents, without the need for a conventional preservative ingredient.

DETAILED DESCRIPTION OF THE INVENTION

Unless indicated otherwise, all amounts of composition ingredients expressed in percentage terms are expressed as weight/weight.

The anionic surfactants of the present invention can be made by known methods and, in some cases, are commercially available. For example, Amilite™ GCK-12 is commercially available from Ajinomoto Co., Inc. (Tokyo, Japan). Amilite™ GCK-12 is described by formula I above when R is selected to be cocoyl (derived from coconut oil); X is H; Y is H; and $M^+$ is $K^+$ (i.e., potassium cocoyl glycinate). Lauroyl sarcosine is available from W.R. Grace (Lexington, Mass.) as Hamposyl® L. Lauroyl sarcosine is described by formula I above when R is selected to be lauroyl; X is $CH_3$; Y is H; and $M^+$ is $H^+$. Pationic® 122A is available from RITA, Corp. (Woodstock, Ill.). Pationic® 122A is described by formula II above when $R^1$ is selected to be a $C_9$ saturated hydrocarbon and $M^+$ is $Na^+$.

Preferred anionic fatty acid/amino acid surfactants of formula I include those where R is a $C_{12}$–$C_{18}$ saturated or unsaturated hydrocarbon and $M^+$ is selected from the group consisting of $H^+$; $Na^+$; $K^+$; and triethanolamine.

Preferred anionic surfactants of formula II include those where $R^1$ is a $C_{12}$–$C_{18}$ saturated or unsaturated hydrocarbon and $M^+$ is selected from the group consisting of $H^+$; $Na^+$; $K^+$; and triethanolamine.

In general, the amount of anionic amino acid/fatty acid surfactant of formula I in the compositions of the present invention is from about 0.001 to about 1%, preferably from about 0.01 to about 0.2%. The amount of anionic surfactant of formula II in the compositions of the present invention is from about 0.05 to about 1.5%, preferably about 0.1 to about 1%, and most preferably about 0.1 to about 0.5%. For topical ophthalmic preparations, the concentration of anionic surfactant (formula I or II) should not be so high that it causes severe discomfort.

The preservative systems of the present invention also contain one or more pharmaceutically acceptable antifungal acids selected from the group consisting of boric acid; benzoic acid; salicylic acid; sorbic acid; lactic acid; acetic acid; and pharmaceutically acceptable salts thereof. Boric acid is the most preferred antifungal acid. In general, the amount of antifungal acid present in the compositions of the present invention is from about 0.01 to about 1%, preferably about 0.1 to about 0.6%, and most preferably from about 0.3 to about 0.4%. The antifungal acid component can be added to pharmaceutical compositions in the form of a pharmaceutically acceptable salt.

In addition to the anionic surfactant(s) and antifungal acid(s), the preservative system contains one or more pharmaceutically acceptable chelating agents. Such chelating agents are selected from the group consisting of ethylene diamine tetraacetic acid (EDTA); ethylene glycol-bis-(b-aminoethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EDBA); and pharmaceutically acceptable salts thereof. The most preferred chelating agent is EDTA. The chelating agents can be added to pharmaceutical compositions in the form of a pharmaceutically acceptable salt. For example, EDTA may be added in the form of edetate disodium. In general, the amount of chelating agent present in the compositions of the present invention is from about 0.001 to about 1%, preferably about 0.01 to about 0.2%, and most preferably about 0.01 to about 0.1%.

The preservative system of the present invention can be used in all types of topically administrable pharmaceutical compositions (e.g., solutions, suspensions, emulsions, gels), but is preferably used for topically administrable ophthalmic, otic, nasal or dermal compositions. Most preferred are topically administrable ophthalmic or otic compositions.

The topically administrable pharmaceutical compositions of the present invention optionally comprise, in addition to the preservative system described above, conventional ingredients, provided that the compositions do not contain a conventional preservative. For example, the compositions of the present invention may contain one or more active ingredients (though, in some instances, such as in the case of dry eye products, no drug will be present). Other optional ingredients include, but are not limited to, pharmaceutically acceptable buffers, tonicity agents, drug carriers, sustained-release agents, viscosity modifying agents, comfort-enhancing agents, solubilizing aids, pH adjusting agents, antioxidants and other stabilizing agents.

The active ingredient or ingredients that can be included in the compositions of the present invention include all ophthalmic, dermatological, otic or nasal agents that can be topically applied. For example, such ophthalmic agents include (but are not limited to): anti-glaucoma agents, such as beta-blockers (e.g., betaxolol and timolol), muscarinics (e.g., pilocarpine), prostaglandins, carbonic anhydrase inhibitors (e.g., acetazolamide, methazolamide and ethoxzolamide), dopaminergic agonists and antagonists, and alpha adrenergic receptor agonists, such as para-amino clonidine (also known as apraclonidine) and brimonidine; anti-infectives, such as ciprofloxacin; non-steroidal and steroidal anti-inflammatories, such as suprofen, ketorolac, dexamethasone, rimexolone and tetrahydrocortisol; proteins; growth factors, such as EGF; and anti-allergic agents, such as cromolyn sodium, emedastine and olopatadine. Compositions of the present invention may also include combinations of active ingredients.

Sustained release agents include anionic polyelectrolytes, such as high molecular weight (e.g., 50,000–6,000,000), anionic mucomimetic polymers (e.g., carboxyvinyl polymers, such as Carbopol®, and xanthan gum), polystyrene sulfonic acid polymers, cationic exchange resins (e.g., Amberlite® or Dowex®), and the like.

The following examples are presented to illustrate further various aspects of the present invention, but are not intended to limit the scope of the invention in any respect.

EXAMPLE 1

| Ingredient | Concentration (%) |
| --- | --- |
| Betaxolol HCl | 0.28 |
| Amberlite IRP-69 | 0.25 |
| Carbopol 974P | 0.45 |
| Potassium Cocoyl Glycinate* | 0.03 |
| Boric Acid | 0.4 |
| Mannitol | 4.15 |
| Edetate Disodium | 0.01 |
| Trometamine | q.s. to pH 6.5 |
| Purified Water | q.s. to 100 |

*Amilite GCK-12

Preparation:

0.28 g betaxolol hydrochloride and 0.250 grams of amberlite IRP 69 were stirred in ~25 mL of water for ~15 minutes. To this suspension were added 22.5 g 2% stock slurry of Carbomer 974P, 0.40 g boric acid, 4.15 g mannitol, and 0.01 g disodium EDTA. The pH of the mixture was adjusted to ~6.0 by the addition of 11 mL of 10% tromethamine solution followed by 30 minutes of stirring. 0.15 g Amilite GCK-12 (30% potassium cocoyl glycinate) was then added. Finally, pH is readjusted to 6.5 with 10% tromethamine and the formulation was brought to 100 g by the addition of purified water.

EXAMPLE 2

| Ingredient | Concentration (%) |
| --- | --- |
| Levobetaxolol HCl* | 0.56 |
| Polystyrene Sulfonic Acid (130 kD) | 1.5 |
| N-Lauroyl Sarcosinate** | 0.03 |
| Boric Acid | 0.35 |
| Mannitol | 3.07 |
| Edetate Disodium | 0.01 |
| Tromethamine | q.s. to pH 6.5 |
| Purified Water | q.s. to 100 |

*(S)-Betaxolol
**Hamposyl-L

EXAMPLE 3

| Ingredient | Concentration (%) |
| --- | --- |
| Levobetaxolol HCl | 0.56 |
| Polystyrene Sulfonic Acid | 1.5 |
| Boric Acid | 0.35 |
| Mannitol | 3.07 |
| Potassium Cocoyl Glycinate* | 0.03 |
| Edetate Disodium | 0.01 |
| Tromethamine | q.s. to pH 6.5 |
| Purified Water | q.s. to 100 |

*Amilite GCK-12

EXAMPLE 4

| Ingredient | Concentration (%) |
| --- | --- |
| Betaxolol HCl | 0.28 |
| Sodium Lauroyl Sarcosinate* | 0.03 |
| Carbopol 974P | 0.45 |
| Amberlite IRP-69 | 0.25 |
| Boric Acid | 0.4 |
| Mannitol | 4.15 |
| Edetate Disodium | 0.01 |
| Tromethamine | q.s. to pH 6.5 |
| Purified Water | q.s. to 100 |

*Hamposyl-L

EXAMPLE 5

| Ingredient | Concentration (%) |
| --- | --- |
| Potassium Cocoyl Glycinate* | 0.03 |
| Boric Acid | 0.4 |
| Mannitol | 4.9 |
| Tromethamine | 0.726 |
| Edetate Disodium | 0.01 |
| Purified Water | q.s. to 100 |

*Amilite GCK-12

EXAMPLE 6

| Ingredient | Concentration (%) |
| --- | --- |
| Sodium Lauroyl Sarcosinate* | 0.03 |
| Boric Acid | 0.4 |
| Mannitol | 4.9 |
| Tromethamine | 0.726 |
| Edetate Disodium | 0.01 |
| Purified Water | q.s. to 100 |

*Hamposyl-L

EXAMPLE 7

| Ingredient | Concentration (%) |
| --- | --- |
| Potassium Cocoyl Glycinate* | 0.03 |
| Mannitol | 5 |
| Purified Water | q.s. to 100 |

*Amilite GCK-12

EXAMPLE 8

| Ingredient | Concentration (%) |
| --- | --- |
| Sodium Lauroyl Sarcosinate* | 0.03 |
| Mannitol | 5 |
| Purified Water | q.s. to 100 |

*Hamposyl-L

EXAMPLE 9

| Ingredient | Concentration (%) |
| --- | --- |
| Levobetaxolol HCl | 0.56 |
| Brinzolamide | 1 |
| Polystyrene Sulfonic Acid (500 kD) | 1 |
| Carbopol 974P | 0.35 |
| Mannitol | 3.1 |
| Boric Acid | 0.3 |
| Edetate Disodium | 0.1 |
| Sodium Lauroyl Sarcosinate* | 0.04 |
| Tyloxapol | 0.025 |
| Tromethamine | adjust pH = 6.5 |
| Hydrochloric Acid | adjust pH = 6.5 |
| Purified Water | q.s. to 100 |

*Hamposyl-L

EXAMPLE 10

| Ingredient | Concentration (%) |
| --- | --- |
| Levobetaxolol HCl | 0.56 |
| Brinzolamide | 1 |
| Amberlite IRP-69 | 0.75 |
| Carbopol 974P | 0.3 |
| Mannitol | 4.0 |
| Boric Acid | 0.4 |
| Edetate Disodium | 0.01 |
| Sodium Lauroyl Sarcosinate* | 0.03 |
| Tyloxapol | 0.025 |
| Tromethamine | adjust pH = 6.5 |
| Hydrochloric Acid | adjust pH = 6.5 |
| Purified Water | q.s. to 100 |

*Hamposyl-L

EXAMPLE 11

| Ingredient | Concentration (%) |
| --- | --- |
| Betaxolol HCl | 0.28 |
| Carbopol 974P | 0.45 |
| Potassium Cocoyl Glycinate* | 0.03 |
| Amberlite IRP-69 | 0.25 |
| Mannitol | 4.15 |
| Edetate Disodium | 0.01 |
| Tromethamine | q.s. to pH 6.5 |
| Purified Water | q.s. to 100 |

*Amilite GCK-12

EXAMPLE 12

| Ingredient | Concentration (%) |
| --- | --- |
| Levobetaxolol* HCl | 0.28 |
| Carbopol 974P | 0.2 |
| Amberlite IRP 69 | 0.65 |
| Glycerine | 2 |
| Edetate Disodium | 0.01 |
| Boric Acid | 0.3 |
| Tromethamine/N-Lauroylsarcosine** | 0.04 |
| Tromethamine | q.s. to pH 6.5 |
| Hydrochloric Acid | q.s. to pH 6.5 |
| Purified Water | q.s. to 100 |

*(S)-Betaxolol
**Hamposyl-L (free acid)

COMPARATIVE EXAMPLE 1

| Ingredient | Concentration (%) |
| --- | --- |
| Betaxolol HCl | 0.28 |
| Amberlite IRP-69 | 0.25 |
| Carbopol 974P | 0.45 |
| Boric Acid | 0.4 |
| Mannitol | 4.5 |
| Edetate Disodium | 0.01 |
| Benzalkonium Chloride | 0.01 |
| NaOH and/or HCl | q.s. to pH 6.5 |
| Purified Water | q.s. to 100 |

COMPARATIVE EXAMPLE 2

| Ingredient | Concentration (%) |
| --- | --- |
| Benzalkonium Chloride | 0.01 |
| Mannitol | 5 |
| Purified Water | q.s. to 100 |

COMPARATIVE EXAMPLE 3

| Ingredient | Concentration (%) |
| --- | --- |
| Benzalkonium Chloride | 0.01 |
| Boric Acid | 0.4 |
| Mannitol | 4.9 |
| Tromethamine | 0.726 |
| Edetate Disodium | 0.01 |
| Purified Water | q.s. to 100 |

EXAMPLE 13

Antimicrobial preservative effectiveness was determined using an organism challenge test according to the methods described in the United States Pharmacopeia (USP) and European Pharmacopoeia (Ph.Eur.). Samples were inoculated with known levels of one or more of the following: gram-positive (*Staphylococcus aureus* ATCC 6538) and gram-negative (*Pseudomonas aeruginosa* ATCC 9027 and *Escherichia coli* ATCC 8739) vegetative bacteria, yeast (*Candida albicans* ATCC 10231) and mold (*Aspergillus niger* ATCC 16404). The samples were then pulled at specified intervals to determine if the antimicrobial preservative system was capable of killing or inhibiting the propagation of organisms purposely introduced into the formulation. The rate or level of antimicrobial activity determines compliance with the USP and/or Ph.Eur. preservative efficacy standards for ophthalmic preparations.

The compendial preservative standards for ophthalmic preparations are presented below:

For Bacteria:

| | Log Reduction of Organism Population | | |
| --- | --- | --- | --- |
| Time Pull | USP | Ph.Eur. A | Ph.Eur. B (Min) |
| 6 hours | — | 2 | — |
| 24 hours | — | 3 | 1 |
| 7 days | — | — | 3 |
| 14 days | 3 | — | — |
| 28 days | NI | NR | NI |

For Fungi:

| Time Pull | USP | Ph.Eur. A | Ph.Eur. B (Min) |
| --- | --- | --- | --- |
| 7 days | — | 2 | — |
| 14 days | NI | — | 1 |
| 28 days | NI | NI | NI |

NR = No organisms recovered
NI = No increase at this or any following time pulls
— = No requirement at this time pull The results of the microorganism challenge tests are shown in Tables 1 and 2 below.

TABLE 1

| | Preservative Efficacy Standard | | |
| --- | --- | --- | --- |
| Formulation | USP | Ph. Eur. B (Minimum) | Ph. Eur. A (Target) |
| Example 1 | Pass | Pass | Fail |
| Example 2* | Pass | Pass | Pass |

-continued

| Ingredient | Concentration (%) |
| --- | --- |
| Edetate Disodium | 0.01 |
| Purified Water | q.s. to 100 |

TABLE 1-continued

| Formulation | Preservative Efficacy Standard | | |
| --- | --- | --- | --- |
| | USP | Ph. Eur. B (Minimum) | Ph. Eur. A (Target) |
| Example 3* | Pass | Pass | Pass |
| Example 4 | Pass | Pass | Fail |
| Example 10 | Pass | Pass | Fail |
| Comp. Ex. 1 | Pass | Fail | Fail |

*Projected results based on *S. aureus*, *P. aeruginosa* and *A. niger* data

TABLE 2

| Formulation | Organism (7 day results - log reduction) | | | | |
| --- | --- | --- | --- | --- | --- |
| | S. aureus | P. aeruginosa | E. coli | C. albicans | A. niger |
| Example 5 | >4.8 | +0.4 | 3.5 | 0.7 | 0.5 |
| Example 6 | 4.8 | +1.4 | 1.4 | +0.1 | 0.8 |
| Example 7 | +0.4 | +1.4 | +0.3 | 0.5 | 0.3 |
| Example 8 | 4.8 | +0.8 | 1.7 | 0.1 | 0.5 |
| Example 9 | 5.0 | 5.0 | 4.2 | 1.4 | 2.5 |
| Example 11 | 5.0 | 5.0 | 5.0 | 2.3 | 2.7 |
| Example 12 | 5.0 | 5.0 | — | — | 0.8 |
| Comp. Ex. 2 | 4.8 | 4.7 | 4.9 | 4.7 | 2.5 |
| Comp. Ex. 3 | 4.8 | 4.7 | 4.9 | 4.7 | 3.7 |

The invention in its broader aspects is not limited to the specific details shown and described above. Departures may be made from such details within the scope of the accompanying claims without departing from the principles of the invention and without sacrificing its advantages.

We claim:

1. A preserved topically administrable pharmaceutical composition comprising a preservative system wherein the preservative system consists essentially of i) at least one anionic surfactant, ii) one or more pharmaceutically acceptable antifungal acids and iii) one or more pharmaceutically acceptable chelating agents, wherein the the anionic surfactant is selected from the group consisting of:

$$R-\overset{O}{\underset{}{C}}-\overset{X}{\underset{Y}{N}}-\overset{H}{\underset{}{C}}-\overset{O^-}{\underset{O}{C}} M^+ \quad (I)$$

wherein: $R = C_8-C_{24}$ saturated or unsaturated hydrocarbon;
X=H or $CH_3$;
Y=H, $(CH_2)_4NH_2$ or $(CH_2)_3NHC(NH_2)=N_+H_2$; and
$M^+$=H or a pharmaceutically acceptable salt; and $$R^1-\overset{O}{\underset{}{C}}-O-\overset{H}{\underset{CH_3}{C}}-\overset{O}{\underset{}{C}}-O-\overset{H}{\underset{CH_3}{C}}-\overset{O^-}{\underset{O}{C}} M^+ \quad (II)$$

wherein: $R^1 = C_8-C_{24}$ saturated or unsaturated hydrocarbon; and
$M^+$ is as defined above;
the one or more pharmaceutically acceptable antifungal acids is selected from the group consisting of boric acid; benzoic acid; salicylic acid; sorbic acid; lactic acid; and acetic acid; or a pharmaceutically acceptable salt thereof; and the one or more pharmaceutically acceptable chelating agents is selected from the group consisting of ethylene diamine tetraacetic acid; ethylene glycol-bis-(b-aminoethylether)-N,N,N',N'-tetraacetic acid; 1,2-bis(2-aminophenoxy)ethane-N,N,N',N'-tetraacetic acid; ethylene-N,N'-diglycine; and 2,2'-(ethylendiimino)-dibutyric acid; or a pharmaceutically acceptable salts thereof provided that the composition does not have a cationic preservative.

2. The preserved topically administrable pharmaceutical composition of claim 1 wherein the anionic surfactant (i) is $$R-\overset{O}{\underset{}{C}}-\overset{X}{\underset{Y}{N}}-\overset{H}{\underset{}{C}}-\overset{O^-}{\underset{O}{C}} M^+ \quad (I)$$

wherein: $R = C_8-C_{24}$ saturated or unsaturated hydrocarbon;
X=H or $CH_3$;
Y=H, $(CH_2)_4NH_2$ or $(CH_2)_3NHC(NH_2)=N^+H_2$; and
$M^+$=H or a pharmaceutically acceptable salt.

3. The preserved topically administrable pharmaceutical composition of claim 2 wherein R is a $C_{12}-C_{18}$ saturated or unsaturated hydrocarbon and $M^+$ is selected from the group consisting of $H^+$; $Na^+$; $K^+$; and triethanolamine.

4. The preserved topically administrable pharmaceutical composition of claim 1 wherein the anionic surfactant (i) is $$R^1-\overset{O}{\underset{}{C}}-O-\overset{H}{\underset{CH_3}{C}}-\overset{O}{\underset{}{C}}-O-\overset{H}{\underset{CH_3}{C}}-\overset{O^-}{\underset{O}{C}} M^+ \quad (II)$$

wherein: $R^1 = C_8-C_{24}$ saturated or unsaturated hydrocarbon; and
$M^+$ is as defined above.

5. The preserved topically administrable pharmaceutical composition of claim 4 wherein $R^1$ is a $C_{12}-C_{18}$ saturated or unsaturated hydrocarbon and $M^+$ is selected from the group consisting of $H^+$; $Na^+$; $K^+$; and triethanolamine.

6. The preserved topically administrable pharmaceutical composition of claim 2 wherein the amount of anionic surfactant is from about 0.001 to about 1%.

7. The preserved topically administrable pharmaceutical composition of claim 6 wherein the amount of anionic surfactant is from about 0.01 to about 0.2%.

8. The preserved topically administrable pharmaceutical composition of claim 4 wherein the amount of anionic surfactant is from about 0.05 to about 1.5%.

9. The preserved topically administrable pharmaceutical composition of claim 8 wherein the amount of anionic surfactant is from about 0.1 to about 1%.

10. The preserved topically administrable pharmaceutical composition of claim 9 wherein the amount of anionic surfactant is from about 0.1 to about is 0.5%.

11. The preserved topically administrable pharmaceutical composition of claim 1 wherein the antifungal acid is boric acid or a pharmaceutically acceptable salt thereof.

12. The preserved topically administrable pharmaceutical composition of claim 1 wherein the amount of antifungal acid is from about 0.01 to about 1%.

13. The preserved topically administrable pharmaceutical composition of claim 12 wherein the amount of antifungal acid is from about 0.1 to about 0.6%.

14. The preserved topically administrable pharmaceutical composition of claim 13 wherein the amount of antifungal acid is from 0.3 to about 0.4%.

15. The preserved topically administrable pharmaceutical composition of claim 1 wherein the chelating agent is EDTA or a pharmaceutically acceptable salt thereof.

16. The preserved topically administrable pharmaceutical composition of claim 1 wherein the amount of chelating agent is from about 0.001 to about 1%.

17. The preserved topically administrable pharmaceutical composition of claim 16 wherein the amount of chelating agent is from about 0.01 to about 0.2%.

18. The preserved topically administrable pharmaceutical composition of claim 17 wherein the amount of chelating agent is from about 0.01 to about 0.1%.

19. The preserved topically administrable pharmaceutical composition of claim 1 wherein the composition is selected from the group consisting of an ophthalmic composition and an otic composition.

* * * * *